US006913891B1

(12) United States Patent
Cocks et al.

(10) Patent No.: US 6,913,891 B1
(45) Date of Patent: Jul. 5, 2005

(54) HUMAN MYELOID TERMINAL DIFFERENTIATION RESPONSE GENE

(75) Inventors: Benjamin Graeme Cocks, Palo Alto, CA (US); Janice Au-Young, Berkeley, CA (US); Jeffrey J. Seilhamer, Los Altos Hills, CA (US)

(73) Assignee: Incyte Corporation, Wilmington, DE (US)

( * ) Notice: Subject to any disclaimer, the term of this patent is extended or adjusted under 35 U.S.C. 154(b) by 1116 days.

(21) Appl. No.: 09/208,206

(22) Filed: Dec. 9, 1998

Related U.S. Application Data

(60) Division of application No. 08/602,208, filed on Feb. 15, 1996, now Pat. No. 5,866,332, which is a continuation-in-part of application No. 08/221,531, filed on Feb. 2, 1994, now abandoned.

(51) Int. Cl.[7] .............................................. G01N 33/53

(52) U.S. Cl. ........................... 435/7.1; 530/350; 514/12
(58) Field of Search .......................... 530/350; 514/12; 435/7.1

(56) References Cited

PUBLICATIONS

Abdollahi et al, Oncogene 6: 165 (1991).*
Adams et al., "Sequence Identification of 2,375 Human Brain Genes" *Nature* 355:632–634 (1992) (Accession M77995).
Adams et al. (Direct Submission), GenBank Sequence Database (Accession T33963), National Center for Biotechnology Information, National Library of Medicine, Bethesda, Maryland 20894.
Adams et al. (Direct Submission), GenBank Sequence Database (Accession T35368), National Center for Biotechnology Information, National Library of Medicine, Bethesda, Maryland 20894.
Adams et al. (Direct Submission), GenBank Sequence Database (Accession T29941), National Center for Biotechnology Information, National Library of Medicine, Bethesda, Maryland 20894.
Adams et al. (Direct Submission), GenBank Sequence Database (Accession T35225), National Center for Biotechnology Information, National Library of Medicine, Bethesda, Maryland 20894.
Adams et al. (Direct Submission), GenBank Sequence Database (Accession T35563), National Center for Biotechnology Information, National Library of Medicine, Bethesda, Maryland 20894.
Carrier et al., "Characterization of Human Gadd45, a p53–regulated Protein" *Biol. Chem.* 269 (51) :32672–32677 (1994).
Fornance et al., "Genotoxic–Stress–Response Genes and Growth–Arrest Genes" *Ann New York Acad. Sci.* 663:139–153 (1992).

Hillier et al. (Direct Submission), GenBank Sequence Database (Accession H84533), National Center for Biotechnology Information, National Library of Medicine, Bethesda, Maryland 20894.
Hillier et al. (Direct Submission), GenBank Sequence Database (Accession R63425), National Center for Biotechnology Information, National Library of Medicine, Bethesda, Maryland 20894.
Hillier et al. (Direct Submission), GenBank Sequence Database (Accession R82994), National Center for Biotechnology Information, National Library of Medicine, Bethesda, Maryland 20894.
Hillier et al. (Direct Submission), GenBank Sequence Database (Accession R21918), National Center for Biotechnology Information, National Library of Medicine, Bethesda, Maryland 20894.
Hillier et al. (Direct Submission), GenBank Sequence Database (Accession R22497), National Center for Biotechnology Information, National Library of Medicine, Bethesda, Maryland 20894.
Hillier et al. (Direct Submission), GenBank Sequence Database (Accession R24009), National Center for Biotechnology Information, National Library of Medicine, Bethesda, Maryland 20894.
Hillier et al. (Direct Submission), GenBank Sequence Database (Accession R55161), National Center for Biotechnology Information, National Library of Medicine, Bethesda, Maryland 20894.
Hillier et al. (Direct Submission), GenBank Sequence Database (Accession H44355), National Center for Biotechnology Information, National Library of Medicine, Bethesda, Maryland 20894.
Hillier et al. (Direct Submission), GenBank Sequence Database (Accession T40088), National Center for Biotechnology Information, National Library of Medicine, Bethesda, Maryland 20894.

(Continued)

*Primary Examiner*—James Martinell
(74) *Attorney, Agent, or Firm*—Foley & Lardner LLP

(57) ABSTRACT

The present invention provides polynucleotide and amino acid sequences which encode and identify a novel human myeloid terminal differentiation response gene designated MYD118. The present invention also provides for myd118 antisense molecules. The invention further provides genetically engineered expression vectors and host cells for the production of purified MYD118 polypeptide; antibodies, antagonists and inhibitors of MYD118 polypeptide; and pharmaceutical compositions and methods of treatment based on polynucleotide sequences encoding MYD118 and MYD118 polypeptide. The invention specifically provides for use of the myd118 polynucleotide sequences as a diagnostic composition for the detection of myeloproliferative diseases and leukemias. The invention also relates to therapeutic methods and compositions based upon the nucleotide sequences for myd118. The invention further provides antibodies which specifically bind to MYD118.

4 Claims, 3 Drawing Sheets

OTHER PUBLICATIONS

Hillier et al. (Direct Submission), GenBank Sequence Database (Accession H71592), National Center for Biotechnology Information, National Library of Medicine, Bethesda, Maryland 20894.

Hillier et al. (Direct Submission), GenBank Sequence Database (Accession H83991), National Center for Biotechnology Information, National Library of Medicine, Bethesda, Maryland 20894.

Liebermann et al., "Differentiation Primary Response Genes and Proto–oncogenes as Positive and Negative Regulators of terminal Hematopoietic Cell Differentiation" *Stem Cells* 12:352–369 (1994).

Selvakumaran et al., "The Novel Primary Response Gene MyD118 and the Proto–oncogenes myb, Myc, and bcl–2 Modulate Transforming Growth Factor β1–Induced Apoptosis of Myeloid Leukemia Cells" *Molecular And Cellular Biology* 14 (4) :2352–2360 (1994).

Sudo et al., "2058 Expressed Sequence Tags (ESTs) from a Human Fetal Lung cDNA Library" *Genomics* 24:276–279 (1994) (Accessions D31559 and D310478).

Zhan et al. "The p53–dependent γ–Ray Response of GADD45$^1$" *Cancer Res.* 54:2755–60 (1994).

Zhan et al. "The gadd and MyD Genes Define a Novel Set of Mammalian Genes Encoding Acidic Proteins That Synergistically Suppress Cell Growth" *Molecular and Cellular Biology* 14 (4) :2361–2371 (1994).

Vairapandi, M. et al., "The differentiation primary respnse gene MyD118, related to GADD45, encodes for a nuclear protein which interacts with PCNA and p21$^{WAF1/CIP1}$," *Oncogene*, vol. 12, No. 12, Jun. 20, 1996, p. 2579–2594.

Hillier, L. et al., (Direct Submission), GenBank Sequence Database (Accession AA194908), National Center for Biotechnology Information, National Library of Medicine, Bethesda, Maryland 20894.

* cited by examiner

```
                9              13              27              36              45              54
5'    C  GGA  CTA  CCG  TTG  GTT  TCC  GCA  ACT  TCT  TGG  ATT  ATC  CTC  GCC  AAG  GAC  TTT 63             72              81              90              99             108
      GNA  ATA  TAT  TTT  TCC  GCC  TTT  TCT  GGA  AGG  ATT  TCG  CTG  CTT  CCC  GAA  GGT  CTT 117            126             135             144             153             162
      GGA  CGA  GCG  CTC  TAG  CTC  TGT  GGG  AAG  GTT  TNG  GGC  TCT  CTG  GCT  CGG  ATT  TTG 171            180             189             198             207             216
      GAA  TTT  CTC  CCT  GGG  GAC  TGC  CGT  GGA  GCC  GCA  TCC  ACT  GTG  GAT  TAT  AAT  TGC 225            234             243             252             261             270
      AAC  ATG  ACG  CTG  GAA  GAG  CTC  GTG  GCG  TGC  GAC  AAC  GCG  GCG  CAG  AAG  ATG  CAG
           M    T    L    E    E    L    V    A    C    D    N    A    A    Q    K    M    Q 279            288             297             306             315             324
      ACG  GTG  ACC  GCC  GCG  GTG  GAG  GAG  CTT  TTG  GTG  GCC  GCT  CAG  CGC  CAG  GAT  CGC
      T    V    T    A    A    V    E    E    L    L    V    A    A    Q    R    Q    D    R 333            342             351             360             369             378
      CTC  ACA  GTG  GGG  GTG  TAC  GAG  TCG  GCC  AAG  TTG  ATG  AAT  GTG  GAC  CCA  GAC  AGC
      L    T    V    G    V    Y    E    S    A    K    L    M    N    V    D    P    D-- S 387            396             405             414             423             432
      GTG  GTC  CTC  TGC  CTC  TTG  GCC  ATT  AAC  GAG  GAG  GAG  GAG  GAT  GAC  ATC  GCC  CTG
      V    V    L    C    L    L    A    I    N    E    E    E    E    D    D    I    A    L 441            450             459             468             477             486
      CAA  ATC  CAC  TTC  ACG  CTC  ATC  CAG  TCC  TTC  TCC  TGT  AAC  AAC  GAC  ATC  AAC  ATC
      Q    I    H    F    T    L    I    Q    S    F    S    C    N    N    D    I    N    I 495            504             513             522             531             540
      GTG  CGG  GTT  TCG  GGC  ATG  CAG  CGC  CTG  GCG  CAG  CTC  CTG  GGA  GAG  CCG  GCC  GAG
      V    R    V    S    G    M    Q    R    L    A    Q    L    L    G    E    P    A    E 549            558             567             576             585             594
      ACC  CAG  GGC  ACC  ACC  GAG  GCC  CGA  GAC  CTG  CAT  TGT  CTC  CTG  GTC  ACG  AAC  CCT
      T    Q    G    T    T    E    A    R    D    L    H    C    L    L    V    T    N    P 603            612             621             630             639             648
      CAC  ACG  GAC  GCC  CGG  AAG  AGC  CAC  GGC  TTG  GTG  GAG  GTG  GCC  AGC  TAC  TGC  GAA
      H    T    D    A    R    K    S    H    G    L    V    E    V    A    S    Y    C    E 657            666             675             684             693             702
      GAA  AGC  CGG  GGC  AAC  AAC  CAG  TGG  GTC  CCC  TAC  ATC  TCT  CTT  CAG  GAA  CGC  TGA
      E    S    R    G    N    N    Q    W    V    P    Y    I    S    L    Q    E    R 711            720             729             738             747
      GGC  CTT  CCC  AGC  AGC  AGA  ATC  TGT  TTG  AGT  TGC  TGC  CAC  AAC  CAA    3'
```

FIGURE 1

```
       |       10         20         30         40
   1   M T L E E L V A C D N A A Q K M Q T V T A A V E E L L V A A Q R Q D R L T V G V    25214 cDNA#1.AMI
   1   M T L E E L V A S D N A V Q K M Q A V T A A V E Q L L V A A Q R Q D R L T V G V    MMMYD118
   1   M T L E E F S A G E Q K T E R M D K V G D A L E E V L S K A L S Q R T I T V G V    HUMGADD45

|       50         60         70         80
  41   Y E S A K L M N V D P D S V V L C L L A I N E E E E D D I A L Q I H F T L I Q S    25214 cDNA#1.AMI
  41   Y E A A K L M N V D P D S V V L C L L A I D E E E E D D I A L Q I H F T L I Q S    MMMYD118
  41   Y E A A K L L N V D P D N V V L C L L A A D D D D R D V A L Q I H F T L I Q A      HUMGADD45

|       90        100        110        120
  81   F S C N N D I N I V R V S G M Q R L A Q L L - - - - - G E P A E T Q G T T E A R    25214 cDNA#1.AMI
  81   F C C D N D I D I Y R V S G M Q R L A Q L L - - - - - G E P A E T L G T T E A R    MMMYD118
  81   F C C E N D I N I L R V S N P G R L A E L L L L E T D A G P A A S E G A E Q P P    HUMGADD45

|      130        140        150        160
 116   D L H C L L V T N P H T D A R K S H G L V E V A S Y C E E S R G N N Q W V P Y I    25214 cDNA#1.AMI
 116   D L H C L L V T N C H T D S W K S Q G L V E V A S Y C E E S R G N N Q W V P Y I    MMMYD118
 121   D L H C V L V T N P H S S Q K D P A L S Q L I C F C R E S R Y M D Q W V P V I      HUMGADD45

156   S L Q E R    25214 cDNA#1.AMI
 156   S L E E R    MMMYD118
 161   N L P E R    HUMGADD45
```

FIGURE 2

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
    (A) LENGTH: 745 base pairs
    (B) TYPE: nucleic acid
    (C) STRANDEDNESS: single
    (D) TOPOLOGY: linear (ii) MOLECULE TYPE: cDNA (vii) IMMEDIATE SOURCE:
    (A) LIBRARY: Myeloid Terminal (xi) SEQUENCE DESCRIPTION: SEQ ID NO: 1:

```
CGGACTACCG TTGGTTTCCG CAACTTCTTG GATTATCCTC GCCAAGGACT TTGNAATATA     60

TTTTTCCGCC TTTTCTGGAA GGATTTCGCT GCTTCCCGAA GGTCTTGGAC GAGCGCTCTA    120

GCTCTGTGGG AAGGTTTNGG GCTCTCTGGC TCGGATTTTG GAATTTCTCC CTGGGGACTG    180

CCGTGGAGCC GCATCCACTG TGGATTATAA TTGCAACATG ACGCTGGAAG AGCTCGTGGC    240

GTGCGACAAC GCGGCGCAGA AGATGCAGAC GGTGACCGCC GCGGTGGAGG AGCTTTTGGT    300

GGCCGCTCAG CGCCAGGATC GCCTCACAGT GGGGGTGTAC GAGTCGGCCA AGTTGATGAA    360

TGTGGACCCA GACAGCGTGG TCCTCTGCCT CTTGGCCATT AACGAGGAGG AGGAGGATGA    420

CATCGCCCTG CAAATCCACT TCACGCTCAT CCAGTCCTTC TCCTGTAACA ACGACATCAA    480

CATCGTGCGG GTTTCGGGCA TGCAGCGCCT GGCGCAGCTC CTGGGAGAGC CGGCCGAGAC    540

CCAGGGCACC ACCGAGGCCC GAGACCTGCA TTGTCTCCTG GTCACGAACC CTCACACGGA    600

CGCCCGGAAG AGCCACGGCT TGGTGGAGGT GGCCAGCTAC TGCGAAGAAA GCCGGGGCAA    660

CAACCAGTGG GTCCCCTACA TCTCTCTTCA GGAACGCTGA GGCCTTCCCA GCAGCAGAAT    720

CTGTTTGAGT TGCTGCCACA ACCAA                                          745
```

(2) INFORMATION FOR SEQ ID NO: 2:

(i) SEQUENCE CHARACTERISTICS:
    (A) LENGTH: 160 amino acids
    (B) TYPE: amino acid
    (C) STRANDEDNESS: single
    (D) TOPOLOGY: linear (ii) MOLECULE TYPE: peptide (vii) IMMEDIATE SOURCE:
    (A) LIBRARY: Myeloid Terminal (xi) SEQUENCE DESCRIPTION: SEQ ID NO: 2:

```
Met Thr Leu Glu Glu Leu Val Ala Cys Asp Asn Ala Ala Gln Lys Met
  1               5                  10                  15

Gln Thr Val Thr Ala Ala Val Glu Glu Leu Leu Val Ala Ala Gln Arg
             20                  25                  30

Gln Asp Arg Leu Thr Val Gly Val Tyr Glu Ser Ala Lys Leu Met Asn
         35                  40                  45

Val Asp Pro Asp Ser Val Val Leu Cys Leu Leu Ala Ile Asn Glu Glu
     50                  55                  60

Glu Glu Asp Asp Ile Ala Leu Gln Ile His Phe Thr Leu Ile Gln Ser
 65                  70                  75                  80
```

```
Phe Ser Cys Asn Asn Asp Ile Asn Ile Val Arg Val Ser Gly Met Gln
                85                  90                  95

Arg Leu Ala Gln Leu Leu Gly Glu Pro Ala Glu Thr Gln Gly Thr Thr
            100                 105                 110

Glu Ala Arg Asp Leu His Cys Leu Val Thr Asn Pro His Thr Asp
        115                 120                 125

Ala Arg Lys Ser His Gly Leu Val Glu Val Ala Ser Tyr Cys Glu Glu
        130                 135                 140

Ser Arg Gly Asn Asn Gln Trp Val Pro Tyr Ile Ser Leu Gln Glu Arg
145                 150                 155                 160
```

(2) INFORMATION FOR SEQ ID NO: 3:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: Myeloid Terminal (xi) SEQUENCE DESCRIPTION: SEQ ID NO: 3:

```
Met Thr Leu Glu Glu Phe Ser Ala Gly Glu Gln Lys Thr Glu Arg Met
1               5                   10                  15

Asp Lys Val Gly Asp Ala Leu Glu Glu Val Leu Ser Lys Ala Leu Ser
            20                  25                  30

Gln Arg Thr Ile Thr Val Gly Val Tyr Glu Ala Ala Lys Leu Leu Asn
        35                  40                  45

Val Asp Pro Asp Asn Val Val Leu Cys Leu Leu Ala Ala Asp Glu Asp
    50                  55                  60

Asp Asp Arg Asp Val Ala Leu Gln Ile His Phe Thr Leu Ile Gln Ala
65                  70                  75                  80

Phe Cys Cys Glu Asn Asp Ile Asn Ile Leu Arg Val Ser Asn Pro Gly
                85                  90                  95

Arg Leu Ala Glu Leu Leu Leu Glu Thr Asp Ala Gly Pro Ala Ala
            100                 105                 110

Ser Glu Gly Ala Glu Gln Pro Pro Asp Leu His Cys Val Leu Val Thr
        115                 120                 125

Asn Pro His Ser Ser Gln Trp Lys Asp Pro Ala Leu Ser Gln Leu Ile
        130                 135                 140

Cys Phe Cys Arg Glu Ser Arg Tyr Met Asp Gln Trp Val Pro Val Ile
145                 150                 155                 160

Asn Leu Pro Glu Arg
                165
```

(2) INFORMATION FOR SEQ ID NO: 4:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: Myeloid Terminal -continued (xi) SEQUENCE DESCRIPTION: SEQ ID NO: 4:

```
Met Thr Leu Glu Glu Leu Val Ala Ser Asp Asn Ala Val Gln Lys Met
 1               5                  10                  15

Gln Ala Val Thr Ala Ala Val Glu Gln Leu Leu Val Ala Ala Gln Arg
            20                  25                  30

Gln Asp Arg Leu Thr Val Gly Val Tyr Glu Ala Ala Lys Leu Met Asn
            35                  40                  45

Val Asp Pro Asp Ser Val Val Leu Cys Leu Leu Ala Ile Asp Glu Glu
 50                  55                  60

Glu Glu Asp Asp Ile Ala Leu Gln Ile His Phe Thr Leu Ile Gln Ser
65                  70                  75                  80

Phe Cys Cys Asp Asn Asp Ile Asp Ile Val Arg Val Ser Gly Met Gln
                85                  90                  95

Arg Leu Ala Gln Leu Leu Gly Glu Pro Ala Glu Thr Leu Gly Thr Thr
                100                 105                 110

Glu Ala Arg Asp Leu His Cys Leu Leu Val Thr Asn Cys His Thr Asp
            115                 120                 125

Ser Trp Lys Ser Gln Gly Leu Val Glu Val Ala Ser Tyr Cys Glu Glu
    130                 135                 140

Ser Arg Gly Asn Asn Gln Trp Val Pro Tyr Ile Ser Leu Glu Glu Arg
145                 150                 155                 160
```

HUMAN MYELOID TERMINAL DIFFERENTIATION RESPONSE GENE

RELATED APPLICATIONS

The present invention is a division of Ser. No. 08/602,208, filed Feb. 15, 1993, now U.S. Pat. No. 5,866,332, which is a continuation application of U.S. application Ser. No. 08/221,531 filed Feb. 2, 1994, now abandoned which is incorporated herein by reference in its entirety.

FIELD OF THE INVENTION

The present invention relates to nucleic acid and amino acid sequences of a novel human myeloid terminal differentiation response gene found in cDNA libraries made from human fetal liver/spleen tissue and non-adherent peripheral blood mononuclear cells and to the use of these sequences in the diagnosis, study and treatment of disease.

BACKGROUND

Cell numbers are regulated by a balance among proliferation, growth arrest and programmed cell death (apoptosis). (Formace et al. 1992 Ann New York Acad. Sci. 663:139–153). Genes induced by various growth arrest and aptotic stimuli are the tumor suppressor gene p53, myeloid differentiation primary response genes (MyD genes), and growth arrest and DNA damage inducible genes (GADD genes) (Selvakumaran et al. 1994 Mol. Cell. Biol. 14:2352–2360).

Animal cells respond to differentiation signals which turn on or off the appropriate genes resulting in conversion of proliferating, undifferentiating cells into nonproliferating, highly specialized differentiated cells. An example of this process is the differentiation of myeloid precursor cells into mature granulocytes and macrophages. Blocks in the differentiation process appear to be a major step in tumor progression and lesions in genes involved in terminal differentiation contribute to the development of malignant tumors (Liebermann et al. 1994 Stem Cells 12:352–69).

Liebermann et al. suggest that MyD genes function as positive regulators of terminal hematopoietic cell differentiation, which is associated with inhibition of cell growth and apoptosis. Selvakumaran et al. supra provide evidence that MyD family member, murine MYD118, described as a terminal differentiation response gene, is expressed in M1D+ myeloid precursor cells following induction of terminal differentiation and growth arrest by IL6 and has been shown to be a positive regulator of apoptosis induced by TGFβ1. Additionally, leucine zipper transcription factors of the fos/jun family have been identified as MyD genes, specifically MyD21, MyD42 and MyD63, and function as positive regulators of hematopoietic cell differentiation, increasing the differentiation of myeloblastic leukemia cells in vitro and reducing the aggressiveness of the leukemic phenotype in nude mice. Liebermann et al. supra suggest that lesions in the MyD genes of the fos/jun family that affect expression or function of the genes contribute to development of leukemias.

The cDNA sequence and deduced amino acid sequence of murine MYD118 is disclosed in Abdollahi et al. (1991 Oncogene 6:165–167) who indicate that the cDNA nucleotide sequence of murine MyD118 predicts a protein of 160 amino acids, which does not contain protein secretory signals, transmembrane domains or known protein-DNA binding motifs, but does appear to contain a protein kinase phosphorylation site at position 204, two casein kinase II phosphorylation sites at positions 215 and 231 and several $AT_3$ motifs in its 3' untranslated region. Abdollahi et al. observed detectable levels of myd118 RNA in myeloid precursor enriched murine bone marrow, but not in several other non-myeloid murine tissues, such as liver or brain. Abdollahi et al. also observed that myd118 expression was induced in the absence of protein synthesis, following stimulation of M1D+ cells by IL-1, LPS and leukemia inhibitory factor (LIF).

The amino acid sequence for murine MYD118 is 75% similar (57% identical) to the amino acid sequence for murine GADD gene, GADD45, which is regulated in part by the tumor suppressor gene p53 (Zhan et al. 1994 Cancer Res. 54: 2755–60 and Carrier et al. J. Biol. Chem. 269:32672–32677). GADD and MYD118 are two separate but closely related genes and act synergistically to suppress growth of hematopoietic cell lineages.

Various portions of the nucleotide sequence encoding human MYD118 have been disclosed in the EST 1 and 2 database (version 92) of Genbank in cDNA libraries made from tissue from hippocampus (accession number M77995), retina (accession number H84533 and H83991), olfactory epithelium (accession number H71592), human fetal lung (accession number D310470 and D31559), breast (accession number H44355, R55161 and R82994), placenta (accession number R24009, R63425, R21918 and R22497), human white blood cells (accession number T33963), human brain (accession number T35368), human pancreas (accession number T29941), liver (accession number T40088), prostate gland (accession number T35225) and lung (accession number T35563). The complete nucleotide sequence encoding human MYD118 has not been disclosed.

Myeloproliferative diseases and leukemias are neoplasms of the hematopoietic stem cell and include acute lymphocytic leukemia (ALL), acute myelogenous leukemia (AML), chronic lymphocytic leukemia (CLL), hairy cell leukemia and chronic myelogenous leukemia (CML); polycythemia vera (PV); agnogenic myeloid metaplasia with myelofibrosis (AMM/MF); and essential thrombocytosis (ET). Research suggests that the myeloproliferative diseases arise as clonal expansions of a single transformed stem cell and that all of the myeloid cells of the blood are derived from the neoplastic clone. In leukemia, leukemic cells proliferate primarily in the bone marrow and lymphoid tissues and are characterized according to the cell type involved (myeloid or lymphoid). Acute leukemia is characterized by proliferation of immature myeloid or lymphoid cells. CLL is a hematologic neoplasm characterized by the accumulation of mature-appearing lymphocytes in the peripheral blood associated with infiltration of the bone marrow. Hairy cell leukemia is characterized by peripheral blood cytopenias, splenomegaly and malignant cells in the blood and bone marrow. CML is characterized by marked splenomegaly and the production of increased numbers of granulocytes, particularly neutrophils, in the marrow and blood. PV is characterized by splenomegaly and an increased production of all myeloid elements, but is dominated by an elevated hemoglobin concentration. AMM/MF is characterized by the tendency of the neoplastic stem cells to lodge and grow in multiple sites outside the marrow, progressive splenomegaly, the gradual replacement of marrow elements by fibrosis, and variable changes in the number of granulocytes and platelets. ET is characterized by an elevated platelet count and represents the overproduction of platelets in the absence of a recognizable stimulus. In cultures of bone marrow cells from individuals subject to ET, colonies of megakaryocytes from megakaryocyte progenitors form in the absence of added stimulus, whereas such colonies do not occur with marrow cell cultures from normal individuals. (*Harrison's Principles of Internal Medicine,* 1987 11th edition, Braunwald et al. Editors, McGraw-Hill Book Company, New York City).

SUMMARY

The present invention relates to human MYD118 whose nucleic acid sequence has been identified among the polynucleotide sequences of cDNA libraries made from human fetal liver-spleen tissue and non-adherent peripheral blood mononuclear cells and to the use of the nucleic acid and amino acid sequences of MYD118 in the study, diagnosis and treatment of disease states related to proliferation, specifically myeloproliferative diseases and leukemias.

The nucleic acid sequence of myd118 (SEQ ID NO:1) and the protein it encodes, MYD118 (SEQ ID NO:2) is disclosed herein in FIG. 1. The amino acid homology among human MYD118, murine MYD118 (SEQ ID NO:3) and human GADD 45 (SEQ ID NO:4) is shown in FIG. 2.

The present invention is based in part on the amino acid homology that human MYD118 shares with murine MYD118 and the ability of murine MYD118 and other MYD family members to stimulate terminal differentiation of hematopoietic cells, to arrest cell growth and to modulate the leukemic phenotype in vivo. The present invention is also based in part on the presence of nucleic acid sequences encoding MYD118 in a cDNA library made from fetal liver/spleen tissue and non-adherent peripheral blood mononuclear cells, where hematopoietic cells would be expected to be found. Nucleic acid sequences encoding MYD118 are not detected in samples of cDNA libraries made from malignant hematopoietic cells sources where expression of genes related to cell growth arrest and apoptosis may be absent, aberrant, deleted or expressed at low levels.

Therefore, expression of human MYD118 may be altered, absent or at low levels in individuals subject to myeloproliferative disease and leukemias. Human MYD118, and nucleic acid sequences that encode it and oligonucleotides, peptide nucleic acid (PNA), fragments, portions or antisense molecules thereof, provide the basis for diagnostic methods for the early and accurate detection and/or quantitation of MYD118 associated with abnormally proliferating hematopoietic cells such as, myeloproliferative diseases and leukemias, including but not limited to acute lymphocytic leukemia (ALL), acute myelogenous leukemia (AML), chronic lymphocytic leukemia (CLL), hairy cell leukemia, chronic myelogenous leukemia (CML); polycythemia vera (PV); agnogenic myeloid metaplasia with myelofibrosis (AMM/MF); and essential thrombocytosis (ET). For example, the nucleotide sequence for myd118 disclosed herein, or fragments thereof, may be used in hybridization assays of biopsied cells or tissues or bodily fluids to diagnose abnormalities in myd118 gene expression in individuals subject to or at risk for a myeloproliferative disease or leukemia. Myd118 gene expression may be present at low levels, entirely absent or altered in such a disease states. Additionally, there may be a chromosomal aberration, such as a deletion or mutation, present in the region of the gene encoding MYD118 in disease states related to proliferation of hematopoietic cells.

The nucleotide and amino acid sequences encoding MYD118 may also be used in the diagnosis and treatment of other disease states related to abnormal proliferation of cells including severe inflammation, such as rheumatoid arthritis, psoriasis (characterized by proliferation of epidermal cells) and lymphomatoid granulomatosis (characterized as a lymphoproliferative disease) where it would be desirable to terminally differentiate proliferating cells and arrest their growth.

Accordingly, the present invention provides diagnostic compositions and diagnostic tests for the detection of myd118 nucleotide sequences in biological samples. Such a diagnostic test comprises the steps of combining the biological sample with a first nucleotide sequence which comprises an myd118 nucleotide sequence, or a non-conserved fragment thereof, under conditions suitable for the formation of a nucleic acid hybridization complex; detecting said hybridization complex, wherein the presence of said complex correlates with the presence of a second nucleotide sequence comprising myd118 nucleotide sequences in said biological sample; and comparing the amount of the second nucleotide sequence in said sample with a standard thereby determining whether the amount of said second nucleotide sequence varies from said standard, wherein the presence of an abnormal level of said second nucleotide sequence correlates positively with a myeloproliferative disease. An abnormal level of nucleotide sequences encoding MYD118 in a biological sample may reflect a chromosomal aberration, such as a nucleic acid deletion or mutation. Accordingly, nucleotide sequences encoding MYD118 provide the basis for probes which can be used diagnostically to detect chromosomal aberrations such as deletions, mutations or chromosomal translocations in the gene encoding MYD118.

The present invention also provides a diagnostic test for the detection of myd118 nucleotide sequences in a biological sample, comprising the steps of combining the biological sample with polymerase chain reaction primers under conditions suitable for nucleic acid amplification, wherein said primers comprise non-conserved fragments of the nucleotide sequence of SEQ ID NO:1, detecting amplified nucleotide sequences, and comparing the amount of amplified nucleotide sequences in said biological sample with a standard thereby determining whether the amount of said nucleotide sequence varies from said standard, wherein the presence of an abnormal level of said nucleotide sequence correlates positively with a myeloproliferative disease.

Additionally, human MYD118 and the nucleic acid sequences that encode it will provide the basis forpharmceutical compositions for the treatment of myeloproliferative diseases, such as ALL, AML, CLL, hairy cell leukemia, CML, PV, AMM/MF and ET. For example, nucleotide sequences that encode MYD118 can be administered alone or in combination with nucleotide sequences encoding tumor suppressor genes, such as p53 (known to regulate the expression of related family member GADD45), p16 and p21, through gene therapy techniques to individuals with CML to induce terminal differentiation of granulocytes, thereby arresting leukemic cell proliferation.

Alternatively, myd118 nucleic acid antisense molecules or antagonist of MYD118 protein may be used to block the activity of human MYD118 in conditions where it would be preferable to block positive regulators of cell growth arrest. For example, MYD118 may be used alone or in combination with other agents in the ex vivo culturing of hematopoietic stem cells intended for autologous transplant to individuals lacking cells of the hematopoietic lineage such as, for example, individuals subject to HIV infection or individuals who have undergone chemotherapy or radiation therapy.

The present invention also relates, in part, to expression vectors and host cells comprising polynucleotide sequences encoding MYD118 for the in vivo or in vitro production of MYD118 protein.

Additionally, the present invention relates to the use of MYD118 polypeptides, or fragments or variants thereof, to produce anti-MYD118 antibodies and to screen for antagonists or inhibitors of MYD118 polypeptides which can be used diagnostically to detect and quantitate MYD118 protein levels in disease states related to proliferation.

The present invention further relates to methods of treating individuals subject to myeloproliferative disease comprising administering compositions comprising purified MYD118 polypeptides or variants thereof, to subjects at risk for or having myeloproliferative disease or leukemia.

The present invention also relates to pharmaceutical compositions comprising effective amounts of MYD118 protein or nucleic acid encoding MYD118 for the treatment of myeloproliferative diseases or leukemias.

The present invention also encompasses the use of gene therapy methods for the introduction of MYD118 encoding nucleotide sequences into individuals having or at risk for myeloproliferative diseases, or leukemias.

The invention further provides diagnostic assays and kits for the detection of MYD118 in cells and tissues comprising purified MYD118 which may be used as a positive control, and anti-MYD118 antibodies. Such antibodies may be used in solution-based, membrane-based, or tissue-based technologies to detect any disease state or condition related to the expression of MYD118 protein or expression of deletions or variants thereof.

DESCRIPTION OF THE FIGURES

FIG. 1 displays the polynucleotide (SEQ ID NO:1) and deduced amino acid (SEQ ID NO:2) sequence for MyD118. Sequences shown in this Figure were produced using the multisequence alignment program of DNASTAR software (DNASTAR Inc, Madison Wis.). SEQ ID NO:1 also contains untranslated 5' and 3' regions of MYD118.

FIG. 2 displays the amino acid alignment of human MyD118 (SEQ ID NO:2), murine MyD118(SEQ ID NO:3) and human GADD45 (SEQ ID NO: 4). Box residues match the consensus sequence exactly.

DETAILED DESCRIPTION OF THE INVENTION

Figure 3:
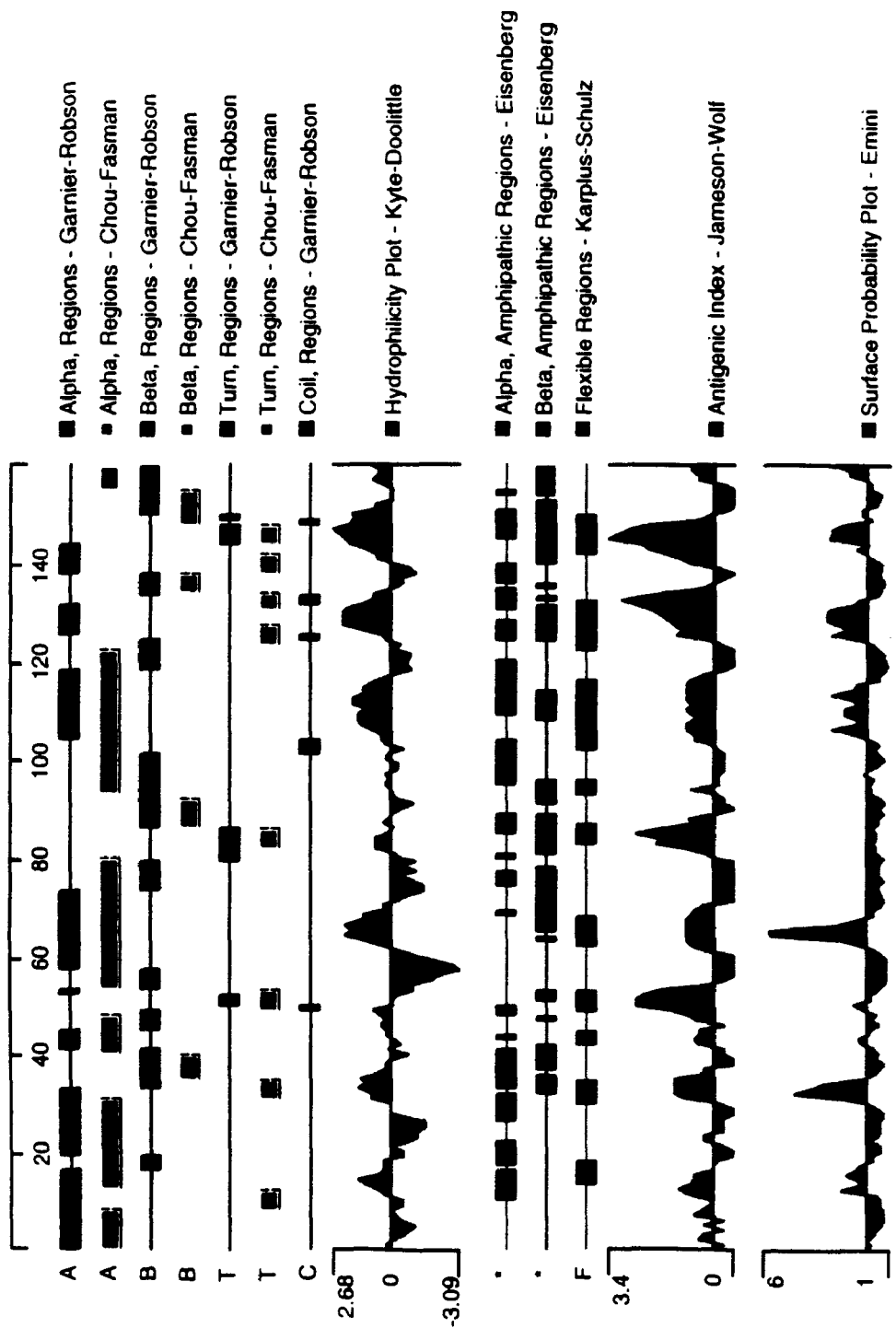
FIG. 3 displays an analysis of the hydrophobicity characteristics of MyD118 based on the predicted amino acid sequence and comparison.

The present invention relates to human MYD118 and to the use of the nucleic acid and amino acid sequences of MYD118 in the study, diagnosis and treatment of disease states, specifically myeloproliferative diseases and leukemias.

The present invention is based in part on the amino acid homology that human MYD118 shares with murine MYD118 and the ability of murine MYD118 and other MYD family members to stimulate terminal differentiation of hematopoietic cells, to arrest cell growth and to reduce a leukemic phenotype in vivo. The present invention is also based in part on the presence of nucleic acid sequences encoding MYD118 in a cDNA library made from fetal liver/spleen tissue and non-adherent peripheral blood mononuclear cells, where hematopoietic cells would be expected to be found. Nucleic acid sequences encoding MYD118 were not detected in randomly selected samples of about 500 to 5700 usable sequences in cDNA libraries made from THP-1 cells, the human promonocyte line derived from the peripheral blood of an individual subject to acute monocytic leukemia (ATCC accession number TIB 202; INCYTE libraries THP1NOB01, THP1PEB01, THP1PLB01 and THP1PLB02); U937 cells, made from malignant cells from the pleural effusion of an individual subject to histiocytic lymphoma (ATCC accession number CRL 1593; Sundstrom et al. 1976 Int. J. Cancer 17:565–577; INCYTE library U937NOT01); T/B lymphoblasts from a leukemia source (Stratagene number STR 937214; INCYTE library TBLYNOT01); peripheral blood white blood cells from an individual with myelogenous leukemia (INCYTE library AMLBNOT01); and a human mast cell line from an individual subject to mast cell leukemia (INCYTE library HMC1NOT01) where expression of genes related to cell growth arrest and apoptosis may be absent or aberrant. Nucleic acid sequences encoding MYD118 were not detected in a cDNA library from peripheral blood granulocytes (INCYTE library NEUTFMT01); pooled bone marrow samples (INCYTE library BMARNOR02); ataxia telangiectasia fibroblast cell line (INCYTE libraries FIBRAGT01, FIBRAGT02 and FIBRANT01) and adult spleen (INCYTE library SPLNNOT02). MYD118 related family member, GADD45, is known to be absent in individuals subject to ataxia telangiectasia (Zhan et al. 1994 Mol. and Cell. Biol. 14:2361–2371).

Therefore, expression of human MYD118 may be altered, absent or not detected in individuals subject to myeloproliferative disease and leukemias. Additionally, the gene encoding MYD118 may be involved in a chromosomal aberration such as a deletion, mutation ie, a point or internal mutation, translocation or may contain tri-nucleotide repeats known to be present in chromosomal abnormalities. Human MYD118, and nucleic acid sequences that encode it and oligonucleotides, peptide nucleic acid (PNA), fragments, portions or antisense molecules thereof, provide the basis for diagnostic methods for the early and accurate detection and/or quantitation of MYD118 associated with myeloproliferative diseases and leukemias, such as acute lymphocytic leukemia (ALL), acute myelogenous leukemia (AML), chronic lymphocytic leukemia (CLL), hairy cell leukemia, chronic myelogenous leukemia (CML); polycythemia vera (PV); agnogenic myeloid metaplasia with myelofibrosis (AMM/MF); and essential thrombocytosis (ET). For example, the nucleotide sequence for myd118 disclosed herein, or fragments thereof, may be used in hybridization assays of biopsied cells or tissues to diagnose abnormalities in myd118 gene expression in individuals with or at risk for a myeloproliferative disease or leukemias. Myd118 gene expression may be present at low levels, entirely absent or altered in such disease states.

Furthermore, the nucleic acid sequences disclosed herein may be used in the detection of aberrations, such as mutations and deletions, in the gene encoding MYD118. For example, the nucleotide sequences disclosed herein may be used to identify and isolate a genomic sequence for MYD118. PCR primers can be designed from various portions of the introns and exons of the genomic MYD118 that will allow detection of aberrations in the genomic sequence.

Additionally, human MYD118 and the nucleic acid sequences that encode it will provide the basis for pharmaceutical compositions for the treatment of myeloproliferative diseases, such as ALL, AML, CLL, hairy cell leukemia, CML, PV, AMM/MF and ET. For example, nucleic acid sequences that encode MYD118 can be administered to individuals subject to CML or AMM to induce terminal differentiation of granulocytes, thereby arresting cell proliferation. Administration of MYD118 or nucleic acid sequences that encode it may alleviate the symptoms associated with myeloproliferative diseases and leukemias, such as anemia, fatigue, splenomegaly, hypermetabolism and thrombohemorrhagic complications.

Alternatively, myd118 nucleic acid antisense molecules or antagonist of MYD118 protein may be used to block the activity of human MYD118 in conditions where it would be preferably to block positive regulators of cell growth arrest. For example, MYD118 may be used alone or in combination with other agents in the ex vivo culturing of hematopoietic stem cells intended for autologous transplant to HIV infected individuals or individuals who have undergone chemotherapy or radiation therapy.

The present invention also relates, in part, to expression vectors and host cells comprising polynucleotide sequences encoding MYD118 for the in vivo or in vitro production of MYD118 protein.

"Nucleic acid sequence" as used herein refers to an oligonucleotide, nucleotide or polynucleotide sequence, and fragments or portions thereof, and to DNA or RNA of genomic or synthetic origin which may be double-stranded or single-stranded whether representing the sense or antisense strand. As used herein "amino acid sequence" refers to peptide or protein sequences or portions thereof. As used herein, lower case myd118 refers to a nucleic acid sequence whereas upper case MYD118 refers to a protein sequence. As used herein, peptide nucleic acid (PNA) refers to a class of informational molecules that have a neutral "peptide like" backbone with nucleobases that allow molecules to hybridize to complementary DNA or RNA with higher affinity and specificity than corresponding oligonucleotides (PerSeptive Biosystems 1-800-899-5858).

As used herein, MYD118 refers to MYD118 from bovine, ovine, porcine, equine and preferably human, in naturally occurring or in variant form, or from any source, whether natural, synthetic, semi-synthetic or recombinant.

As used herein, "naturally occurring" refers to an MYD118 with an amino acid sequence found in nature, and "biologically active" refers to an MYD118 having structural, regulatory or biochemical functions of the naturally occurring MYD118. Likewise, "immunological activity" is defined as the capability of the natural, recombinant or synthetic MYD118 or any oligopeptide thereof, to induce a specific immune response in appropriate animals or cells and to bind with specific antibodies.

The term "derivative" as used herein refers to the chemical modification of MYD118. Illustrative of such modifications would be replacement of hydrogen by an alkyl, acyl, or amino group. An MYD118 polypeptide derivative would encode a polypeptide which retains essential biological characteristics of MYD118.

As used herein, the term "purified" refers to molecules, either nucleic or amino acid sequences, that are removed from their natural environment and isolated or separated from at least one other component with which they are naturally associated.

The MyD118 Coding Sequences.

The nucleotide sequence of myd118 (SEQ ID NO:1) is shown in FIG. 1. The entire coding region for human MYD118 was initially identified within a cDNA library made from human fetal liver/spleen tissue where it was found 1 time in 2899 usable sequences. A BLAST search (Basic Local Alignment Search Tool; Altschul SF (1993) J. Mol. Evol. 36: 290–300; Altschul SF et al (1990) J. Mol. Biol. 215:403–410) comparing the cDNAs of the human fetal liver/spleen library (SPLNFET01) against the primate database of GenBank 91 identified Incyte Clone 25214 as a non-exact match to murine mRNA for myd118 and related family member human gadd45 (NCBI GI number 53291), see FIG. 2. The nucleotide sequence for myd118 was identified within Incyte clone 25214 through a computer generated search for nucleotide sequence alignments. The clone was resequenced, and the coding region determined. Polynucleotide sequences encoding MYD118 were subsequently found in a cDNA library made from non-adherent peripheral blood mononuclear cells (PBMN) where it was found 1 time in 3941 usable sequences. As used herein term "usable sequences" refers to the total number of clones in a library after the removal of vector, nucleotide repeats, contamination, and mitochondrial DNA.

Various portions of the nucleotide sequence encoding MYD118 have been found in the EST Genbank from the following human tissue sources: hippocampus, retina, olfactory epithelium, fetal lung, breast, placenta, white blood cells, brain, pancreas, liver, prostate gland and lung.

Polynucleotide sequences encoding MYD118 have not been detected however, in cDNA libraries made from malignant cells of hematopoietic lineage, including THP-1 cells; U937 cells; T/B lymphoblasts from a leukemia source; peripheral blood white blood cells from an individual with myelogenous leukemia; and human mast cells from an individual with mast cell leukemia. The myd118 nucleotide sequence encodes an acidic protein of 160 amino acids having a predicted isoelectric point of 4.4 and discrete hydrophobic and hydrophilic regions as shown in FIG. 3.

Methods for DNA sequencing are well known in the art and employ such enzymes as the Klenow fragment of DNA polymerase 1, Sequenase® (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Methods to extend the DNA from an oligonucleotide primer annealed to the DNA template of interest have been developed for both single-stranded and double-stranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; MJ Research, Watertown Mass.) and the ABI Catalyst 800 and 377 and 373 DNA sequencers (Perkin Elmer, Norwalk Conn.).

The quality of any particular cDNA library from which polynucleotides encoding MYD118 are found may be determined by performing a pilot scale analysis of the cDNAs and checking for percentages of clones containing vector, lambda or E. coli DNA, mitochondrial or repetitive DNA, and clones with exact or homologous matches to public databases.

Extending Myd118 Polynucleotide Sequence

The polynucleotide sequence of Myd118 may be extended utilizing the nucleotide sequences from SEQ ID NO:1 in various methods known in the art to detect upstream sequences such as promoters and regulatory elements. Gobinda et al (1993; PCR Methods Applic 2:318–22) disclose "restriction-site polymerase chain reaction (PCR)" as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al(1988) Nucleic Acids Res 16:8186). The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR.

Parker J D et al (1991; Nucleic Acids Res 19:3055–60), teach walking PCR, a method for targeted gene walking which permits retrieval of unknown sequence. Promoter-Finder™ is a new kit available from Clontech (Palo Alto Calif.) which uses PCR, nested primers and special libraries to "walk in" genomic DNA. This process avoids the need to screen libraries and is useful in finding intron/exon junctions.

Another PCR method, "*Improved Method for Obtaining Full Length cDNA Sequences*" by Guegler et al, patent application Ser. No. 08/487,112, filed Jun. 7, 1995 and hereby incorporated by reference, employs XL-PCR™ enzymes (Perkin-Elmer, Foster City Calif.) to amplify and/or extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for obtaining introns and extending 5' sequence.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of Myd118

In accordance with the present invention, myd118 polynucleotide sequences which encode MYD118 polypeptide sequences, fragments, fusion proteins or functional equivalents thereof, may be used to generate recombinant DNA molecules that direct the expression of myd118 in appropriate host cells. Due to the inherent degeneracy of the genetic code, DNA sequences other than the polynucleotide sequences of SEQ ID NO:1 which encode substantially the same or a functionally equivalent amino acid sequence, may be used to clone and express myd118. As will be understood by those of skill in the art, it may be advantageous to produce MYD118-encoding nucleotide sequences possessing non-naturally occurring codons. Codons preferred by a particular prokaryotic or eukaryotic host (Murray E et al (1989) Nuc Acids Res 17:) can be selected, for example, to increase the rate of myd118 expression or to produce recombinant RNA transcripts having desirable properties, such as a longer half-life, than transcripts produced from naturally occurring sequence.

Also included within the scope of the present invention are polynucleotide sequences that are capable of hybridizing to SEQ ID NO:1 under conditions of intermediate to maximal stringency as long as the polynucleotide sequence capable of hybridizing encodes a protein that retains a biological activity of the naturally occurring MYD118. Hybridization conditions are based on the melting temperature (Tm) of the nucleic acid binding complex, as taught in Wahl GM et al. (1987, Methods Enzymol 152:399–407) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein refers to "the process by which a strand of nucleic acid joins with a complementary strand through base pairing" (Coombs J (1994) *Dictionary of Biotechnology*, Stockton Press, New York N.Y.). Amplification as carried out in polymerase chain reaction technologies is described in Dieffenbach CW and GS Dveksler (1995, *PCR Primer, a Laboratory Manual*, Cold Spring Harbor Press, Plainview N.Y.) and incorporated herein by reference.

As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring Myd118.

As used herein "substitution" results from the replacement of one or more nucleotides or amino acids by different nucleotides or amino acids, respectively.

Variant myd118 polynucleotide sequences may be used in accordance with the invention and include deletions, insertions or substitutions of different nucleotide residues resulting in a polynucleotide that encodes the same or a functionally equivalent MYD118 polypeptide. Variant MYD118 protein may also be used in accordance with the invention and may include deletions, insertions or substitutions of amino acid residues as long as the result is a functionally equivalent MYD118. As used herein, the term functionally equivalent refers to a variant polynucleotide or variant polypeptide sequence that retains at least one of the biological activities of the naturally occurring sequence. Amino acid substitutions may be made on the basis of similarity in polarity, charge, solubility, hydrophobicity, hydrophilicity, and/or the amphipathic nature of the residues as long as a biological activity of MYD118 is retained. For example, negatively charged amino acids include aspartic acid and glutamic acid; positively charged amino acids include lysine and arginine; and amino acids with uncharged polar head groups having similar hydrophilicity values are grouped as follows: leucine, isoleucine and valine; glycine and alanine; asparagine and glutamine; and lastly, serine, threonine phenylalanine, and tyrosine.

Included within the scope of the present invention are alleles of Myd118. As used herein, an "allele" or "allelic sequence" is an alternative form of Myd118. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of nucleic acids. Each of these types of changes may occur alone, or in combination with the others, and at the rate of one or more times in a given sequence.

The nucleotide sequences of the present invention may be engineered in order to alter an myd118 coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, etc.

In another embodiment of the invention, an myd118 natural, modified or recombinant sequence may be ligated to a heterologous sequence to encode a fusion protein. For example, for screening of peptide libraries for inhibitors of MYD118 activity, it may be useful to encode a chimeric MYD118 protein expressing a heterologous epitope that is recognized by a commercially available antibody. A fusion protein may also be engineered to contain a cleavage site located between an MYD118 sequence and the heterologous protein sequence, so that the MYD118 may be cleaved and purified away from the heterologous moiety.

In an alternate embodiment of the invention, the coding sequence of myd118 could be synthesized, whole or in part, using chemical methods well known in the art (See Caruthers et al (1980) Nuc Acids Res Symp Ser 7:215–233; Crea and Horn (1980) Nuc Acids Res 9:2331; Matteucci and Caruthers (1980) Tetrahedron Lett 21:719; and Chow and Kempe (1981) Nuc Acids Res 9:2807–2817). Alternatively, the protein itself could be produced using chemical methods to synthesize an MYD118 amino acid sequence, whole or in part. For example, peptides can be synthesized by solid phase techniques, cleaved from the resin, and purified by preparative high performance liquid chromatography (eg, Creighton (1983) *Proteins Structures And Molecular Principles*, WH Freeman and Co, New York N.Y.). The composition of the synthetic peptides may be confirmed by amino acid analysis or sequencing (eg, the Edman degradation procedure; Creighton, supra).

Direct peptide synthesis can be performed using various solid-phase techniques (Roberge J Y et al (1995) Science 269:202–204) and automated synthesis may be achieved, for example, using ABI 431A Peptide Synthesizer (Perkin Elmer, Norwalk Conn.) in accordance with the instructions provided by the manufacturer. Additionally the amino acid sequence of MYD118, or any part thereof, may be altered during direct synthesis and/or combined using chemical methods with other sequences to produce a variant polypeptide.

Expression Systems

In order to express a biologically active MYD118, the nucleotide sequence coding for MYD118, or a functional equivalent thereof, is inserted into an appropriate expression vector, ie, a vector which contains the necessary elements for the transcription and translation of the inserted coding sequence. Methods which are well known to those skilled in the art can be used to construct expression vectors containing an MYD118 coding sequence and appropriate transcriptional or translational controls. These methods include in vitro recombinant DNA techniques, synthetic techniques and in vivo recombination or genetic recombination. Such techniques are described in Maniatis et al (1989) *Molecular Cloning, A Laboratory Manual*, Cold Spring Harbor Press, Plainview N.Y. and Ausubel FM et al. (1989) *Current Protocols in Molecular Biology*, John Wiley & Sons, New York N.Y.

Analysis of the functions of growth inhibitory genes, such as myd118, by using expression vectors can be technically difficult, since even low-level expression may block growth of the host cell. Stable transfectants that do grow out are often revertants that have lost expression or have had other compensatory changes (Zhan et al supra). Therefore, a preferred expression system for the expression of MYD118 in host cells is one that allows for expression of proteins toxic to the host cell. For expression in mammalian cells, Zhan et al. supra, page 2366, describe a mammalian expression system for the expression of MYD118 related family members GADD45, which has been shown to be regulated by p53, and murine MYD118. This expression system employs the cytomegalovirus promoter and cotransfection with a selectable marker, pSV2neo. Expression studies were performed in human tumor lines with a null p53 phenotype (H1299), in cells with a normal p53 phenotype (RKO), and in cells containing a viral protein, E6, that interferes with p53 function (HeLa).

For expression of MYD118 in *E. coli*, Brown et al. (Gene 1993, 127:99–103) describe a method that was used for expression of the toxic POL3 gene of *S. cerevisiae* which involves the use of the vector pT7SC. Brown obtained up to 15 mg of protein from as little as 3 grams of cells and the expressed protein was in the form of inclusion bodies.

Identification of Transformants Containing Myd118

Although the presence/absence of marker gene expression suggests that the gene of interest is also present, its presence and expression should be confirmed. For example, if the myd118 is inserted within a marker gene sequence, recombinant cells containing myd118 can be identified by the absence of marker gene function. Alternatively, a marker gene can be placed in tandem with an myd118 sequence under the control of a single promoter. Expression of the marker gene in response to induction or selection usually indicates expression of myd118 as well.

Alternatively, host cells which contain the coding sequence for myd118 and express myd118 may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the myd118 polynucleotide sequence can be detected by DNA-DNA or DNA-RNA hybridization or amplification using probes, portions or fragments of myd118 disclosed in SEQ ID NO:1. Nucleic acid amplification based assays involve the use of oligonucleotides or oligomers based on the myd118 sequence to detect transformants containing myd118 DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer. Preferably, oligonucleotides are derived from the 3' region of the myd18 nucleotide sequence shown in FIG. 1.

A variety of protocols for detecting and measuring the expression of MYD118 polypeptide, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on MYD118 polypeptides is preferred, but a competitive binding assay may be employed. These and other assays are described, among other places, in Hampton R et al (1990, *Serological Methods, a Laboratory Manual*. APS Press, St Paul Minn.) and Maddox DE et al (1983, J Exp Med 158:1211).

A wide variety of labels and conjugation techniques are known by those skilled in the art and can be used in various nucleic and amino acid assays. Means for producing labeled hybridization or PCR probes for detecting myd118 polynucleotide sequences include oligolabeling, nick translation, end-labeling or PCR amplification using a labeled nucleotide. Alternatively, the myd118 sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

Purification of MYD118

Host cells transformed with a myd118 nucleotide sequence may be cultured under conditions suitable for the expression and recovery of the encoded protein from cell culture.

The protein produced by a recombinant cell may be secreted or may be contained intracellularly depending on the sequence and/or the vector used. As will be understood by those of skill in the art, expression vectors containing myd118 can be designed with signal sequences which direct secretion of myd118 through a particular prokaryotic or eukaryotic cell membrane. Other recombinant constructions may join myd118 to nucleotide sequence encoding a polypeptide domain which will facilitate purification of soluble proteins (Kroll D J et al (1993) DNA Cell Biol 12:441–53; see also above discussion of vectors containing fusion proteins).

MYD118 may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath J (1992) Protein Expr Purif 3:263–281), protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and MYD118 is useful to facilitate purification.

Uses of MYD118

MYD118 appears to induce terminal differentiation of hematopoietic cells thereby arresting cell proliferation and inducing apoptosis. Polynucleotide sequences encoding MYD118, or portions thereof, have been found in a variety of cDNA libraries from tissues including fetal liver/spleen, PBMN cells, hippocampus, retina, olfactory epithelium, human fetal lung, breast, placenta, human white blood cells, human brain, human pancreas, liver, prostate gland and lung. Polynucleotide sequences encoding MYD118 are not detected in cDNA libraries made from malignant cells of hematopoietic lineage, where genes related to cell growth arrest and apoptosis would be expected to be expressed at undetectable levels or not expressed at all. Based upon 1) its characterization as an MYD family member, 2) the ability of MYD family members to terminally differentiate cells of a hematopoietic lineage and 3) the ability of related MYD family members to reverse a leukemic phenotype in vivo, human MYD118 disclosed herein may be used as a diagnostic or therapeutic agent in the detection or treatment of proliferative diseases of hematopoietic cells, specifically in myeloproliferative diseases and leukemias.

Accordingly, MYD118 can be used to treat or ameliorate the symptoms of myeloproliferative diseases or leukemias, such as acute lymphocytic leukemia (ALL), acute myelogenous leukemia (AML), chronic lymphocytic leukemia (CLL), hairy cell leukemia, chronic myelogenous leukemia (CML); polycythemia vera (PV); agnogenic myeloid metaplasia with myelofibrosis (AMM/MF); and essential thrombocytosis (ET). MYD118 may be used alone or in combination with other drugs or agents in the treatment of such diseases. For example, administration of MYD118 to individuals subject to myeloproliferative disease, which is characterized by the production of increased numbers of immature cells in the peripheral blood, may induce terminal differentiation of the immature cells thereby leading to the maturation of the cells and eventual apoptosis. Administration of MYD118 may be used to augment chemotherapy, such as administration of busulfan, radiation therapy and/or bone marrow transplant. MYD118 may be used therapeutically to ameliorate the symptoms associated with myeloproliferative diseases and leukemias, such as, anemia, fatigue, splenomegaly hypermetabolism and thrombohemorrhagic complications.

MYD118 may also be used to treat disease states related to abnormal proliferation of cells including severe inflammation, such as rheumatoid arthritis, psoriasis, and lymphomatoid granulomatosis.

In another embodiment of the present invention, antibodies or antagonists of MYD118 may be used in the ex vivo culturing of cells from a hematopoietic cell lineage intended for autologous transplant where it would be desirable to eliminate a cell growth arrest factor that might interfere with desirable cell proliferation.

MYD118 Antibodies

Procedures well known in the art may be used for the production of antibodies to MYD118 polypeptides. Such antibodies include, but are not limited to, polyclonal, monoclonal, chimeric, single chain, Fab fragments and fragments produced by a Fab expression library. Neutralizing antibodies, ie, those which inhibit biological activity of MYD118 polypeptides, are especially preferred for diagnostics and therapeutics.

For the production of antibodies, various hosts including goats, rabbits, rats, mice, etc may be immunized by injection with MYD118 polypeptide or any portion, fragment or oligopeptide which retains immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants which may be employed if purified MYD118 polypeptide is administered to immunologically compromised individuals for the purpose of stimulating systemic defense.

Monoclonal antibodies to MYD118 polypeptide may be prepared using any technique which provides for the production of antibody molecules by continuous cell lines in culture.

These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce MYD118 specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for MYD118 may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W D et al (1989) Science 256:1275–1281).

MYD118-specific antibodies are useful for the diagnosis of conditions and diseases associated with expression of MYD118 polypeptide. A variety of protocols for competitive binding or immunoradiometric assays using either polyclonal or monoclonal antibodies with established specificities are well known in the art. Such immunoassays typically involve the formation of complexes between MYD118 polypeptides and its specific antibody (or similar MYD118-binding molecule) and the measurement of complex formation. A two-site, monoclonal-based immunoassay utilizing monoclonal antibodies reactive to two noninterfering epitopes on a specific MYD118 protein is preferred, but a competitive binding assay may also be employed. These assays are described in Maddox DE et al (1983, J Exp Med 158:1211).

Diagnostic Assays Using Myd118 Specific Antibodies

Anti-MYD118 antibodies are useful for the diagnosis of myeloproliferative disease or leukemias or other conditions, disorders or diseases characterized by abnormal expression of MYD118. Diagnostic assays for MYD118 include methods utilizing the antibody and a label to detect MYD118 polypeptide in human body fluids, cells, tissues or sections or extracts of such tissues. The polypeptides and antibodies of the present invention may be used with or without modification. Frequently, the polypeptides and antibodies will be labeled by joining them, either covalently or noncovalently, with a reporter molecule. A wide variety of reporter molecules are known to those of skill in the art.

A variety of protocols for measuring MYD118 polypeptide, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on MYD118 polypeptide is preferred, but a competitive binding assay may be employed. These assays are described, among other places, in Maddox, D E et al (1983, J Exp Med 158:1211).

In order to provide a basis for the diagnosis of disease, normal or standard values for MYD118 polypeptide expression must be established. This is accomplished by combining body fluids or cell extracts taken from normal subjects, either animal or human, with antibody to MYD118 polypeptide under conditions suitable for complex formation which are well known in the art. The amount of standard complex formation may be quantified by comparing it with a dilution series of positive controls where a known amount of antibody is combined with known concentrations of purified MYD118 polypeptide. Then, standard values obtained from normal samples may be compared with values obtained from samples from subjects potentially affected by a disorder or disease related to MYD118 polypeptide expression. Deviation between standard and subject values establishes the presence of the disease state.

Drug Screening

MYD118 polypeptide, its immunogenic fragments or oligopeptides can be used for screening therapeutic compounds in any of a variety of drug screening techniques. The fragment employed in such a test may be free in solution, affixed to a solid support, borne on a cell surface, or located intracellularly. The abolition of activity or the formation of binding complexes, between MYD118 polypeptide and the agent being tested, may be measured. Accordingly, the present invention provides a method for screening a plurality of compounds for specific binding affinity with MYD118, or a portion thereof, comprising providing a plurality of compounds; combining MYD118 or a portion thereof with each of a plurality of compounds for a time sufficient to allow binding under suitable conditions; and detecting binding of MYD118, or portion thereof, to each of the plurality of compounds, thereby identifying the compounds which specifically bind MYD118.

Another technique for drug screening provides for high throughput screening of compounds having suitable binding affinity to the MYD118 polypeptides and is described in detail in Geysen, European Patent Application 84/03564, published on Sep. 13, 1984, incorporated herein by reference. In summary, large numbers of different small peptide test compounds are synthesized on a solid substrate, such as plastic pins or some other surface. The peptide test compounds are reacted with MYD118 fragments and washed. Bound MYD118 is then detected by methods well known in the art. Purified MYD118 can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding MYD118 specifically compete with a test compound for binding MYD118. In this manner, the antibodies can be used to detect the presence of any peptide which shares one or more antigenic determinants with MYD118.

Uses of Myd118 Polynucleotide

An myd118 polynucleotide, or any part thereof, may be used for diagnostic and/or therapeutic purposes. For diagnostic purposes, myd118 polynucleotide sequences may be used to detect and quantitate gene expression in conditions, disorders or diseases in which Myd118 activity may be implicated, for example in myeloproliferative diseases or leukemias, where myd118 gene expression appears to be absent, aberrant or not detected. For therapeutic purposes, myd118 polynucleotide sequences may be administered to individuals with myeloid proliferative disease or leukemia to induce terminal differentiation of proliferating immature hematopoietic cells origin, thereby arresting cell proliferation, ameliorating the symptoms of disease, and reversing the leukemic phenotype.

Included in the scope of the invention are oligonucleotide sequences, antisense RNA and DNA molecules and ribozymes, which function to inhibit translation of an Myd118. Such nucleotide sequences may be used in conditions where is would be preferable to block positive regulators of cell growth arrest, for example, in ex vivo culturing of cells intended for autologous transplant to individuals lacking cells of the hematopoietic lineage, such as individuals who are immunocompromised due to disease, such as HIV infection, or individuals subject to chemotherapy or radiation therapy which depletes certain cells of hematopoietic lineage.

Another aspect of the subject invention is to provide for nucleic acid hybridization or PCR probes which are capable of detecting polynucleotide sequences, including genomic sequences, encoding myd118 or closely related molecules, such as alleles. The specificity of the probe, ie, whether it is derived from a highly conserved, conserved or non-conserved region or domain, and the stringency of the hybridization or amplification (high, intermediate or low) will determine whether the probe identifies only naturally occurring myd118, or related sequences. Probes for the detection of related nucleic acid sequences are selected from conserved or highly conserved nucleotide regions of myd family members and such probes may be used in a pool of degenerate probes. For the detection of identical nucleic acid sequences, or where maximum specificity is desired, nucleic acid probes are selected from the non-conserved nucleotide regions or unique regions of myd118 polynucleotides. As used herein, the term "non-conserved nucleotide region" refers to a nucleotide region that is unique to myd118 and does not occur in related family members, such as the nucleotide sequence encoding GADD45.

Diagnostic Uses of Myd118 Polynucleotide

An myd118 encoding polynucleotide sequence may be used for the diagnosis of diseases resulting from abnormal expression of myd118 or other genes associated with myeloproliferative disease or leukemia. For example, polynucleotide sequences encoding MYD118 may be used in hybridization or PCR assays of tissues from biopsies or autopsies or biological fluids, such as serum, to detect abnormalities in MYD118 expression. The form of such qualitative or quantitative methods may include Southern or northern analysis, dot blot or other membrane-based technologies; PCR technologies; dip stick, pin or chip technologies; and ELISA or other multiple sample format technologies. All of these techniques are well known in the art, and are in fact the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for myd118 expression must be established. This is accomplished by combining body fluids or cell extracts taken from normal subjects, either animal or human, with myd118 or a portion thereof, under conditions suitable for hybridization or amplification. Standard hybridization may be quantified by comparing the values obtained for normal subjects with a dilution series of positive controls run in the same experiment where a known amount of purified myd118 is used. Standard values obtained from normal samples may be compared with values obtained from samples from subjects potentially affected by a disorder or disease related to myd118 expression. Deviation between standard and subject values establishes the presence of the disease state. If disease is established, an existing therapeutic agent is administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

PCR as described in U.S. Pat. Nos. 4,683,195; 4,800,195; and 4,965,188 provides additional uses for oligonucleotides based upon the myd118 sequence. Such oligomers are generally chemically synthesized, but they may be generated enzymatically or produced from a recombinant source. Oligomers generally comprise two nucleotide sequences, one with sense orientation (5'->3') and one with antisense (3'<-5') employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally methods to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the an oligomer

Therapeutic Uses of an Myd118 Polynucleotide

An myd118 polynucleotide sequence may provide the basis for treatment of various abnormal conditions involving abnormally proliferating cells of hematopoietic lineage, including myeloproliferative diseases and leukemias, such as acute lymphocytic leukemia (ALL), acute myelogenous leukemia (AML), chronic lymphocytic leukemia (CLL), hairy cell leukemia, chronic myelogenous leukemia (CML); polycythemia vera (PV); agnogenic myeloid metaplasia with myelofibrosis (AMM/MF); and essential thrombocytosis (ET), where it would be advantageous to induce terminal differentiation of the proliferating cells thereby arresting cell proliferation. Stable transformation of appropriate germ line cells, or a zygote, with a vector containing polynucleotide sequences encoding MYD118 may produce a transgenic organism (U.S. Pat. No. 4,736,866, 12 Apr. 1988) producing enough copies of the polynucleotide sequence to induce terminal differentiation of cells of hematopoietic lineage, thereby leading to cell growth arrest Such vectors and expression systems intended for in vivo or gene therapy use should be designed for expression of molecules toxic to the host cell as disclosed infra. A preferable expression vector would be one which drives expression of MYD118 at levels comparable to its expression in normal non-proliferating cells.

Alternatively, an myd118 polynucleotide sequence may also provide the basis for design of antisense molecules that are able to inhibit transcription or translation of myd118 in conditions where it would be advantageous to block positive regulators of cell growth arrest, such as for example in ex vivo culturing of cells from a hematopoietic lineage intended for autologous transplant, where proliferation of cells of hematopoietic lineage would be desirable. The introduction of vectors into stem cells taken from a patient and clonally propagated for autologous transplant is described in U.S. Pat. Nos. 5,399,493 and 5,437,994, disclosed herein by reference.

Expression vectors derived from retroviruses, adenovirus, herpes or vaccinia viruses, —or from various bacterial plasmids, may be used for delivery of recombinant myd118, sense or antisense molecules, to the targeted cell population. Methods which are well known to those skilled in the art can be used to construct recombinant vectors containing myd118. See, for example, the techniques described in Maniatis et al (supra) and Ausubel et al(supra). Alternatively, recombinant myd118 can be delivered to target cells in liposomes.

The full length cDNA sequence and/or its regulatory elements enable researchers to use myd118 as a tool in sense (Youssoufian H and H F Lodish 1993 Mol Cell Biol 13:98–104) or antisense (Eguchi et al (1991) Annu Rev Biochem 60:631–652) investigations of gene function. Oligonucleotides, designed from the cDNA or control sequences obtained from the genomic DNA can be used in vitro or in vivo to inhibit expression. Such technology is now well known in the art, and sense or antisense oligonucleotides or larger fragments can be designed from various locations along the coding or control regions.

Additionally, myd118 expression can be modulated by transfecting a cell or tissue with expression vectors which express high levels of an myd118 fragment in conditions where it would be preferably to block the activity of positive regulator of cell growth arrest, such as in bone marrow transplant therapy and ex vivo culturing of cells intended for autologous transplant. Such constructs can flood cells with untranslatable sense or antisense sequences. Even in the absence of integration into the DNA, such vectors may continue to transcribe RNA molecules until all copies of the vector are disabled by endogenous nucleases. Such transient expression may last for a month or more with a non-replicating vector (Mettler I, personal communication) and even longer if appropriate replication elements are part of the vector system.

Modifications of gene expression can be obtained by designing antisense sequences to the control regions of the myd118 gene, such as the promoters, enhancers, and introns. Oligonucleotides derived from the transcription initiation site, eg, between −10 and +10 regions of the leader sequence, are preferred. Antisense RNA and DNA molecules may also be designed to block translation of mRNA by preventing the transcript from binding to ribosomes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of myd118 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may also be evaluated by testing accessibility to hybridization with complementary oligonucleotides using ribonuclease protection assays.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

Methods for introducing vectors into cells or tissue include those methods discussed infra. In addition, several of these transformation or transfection methods are equally suitable for the ax vivo therapy.

Furthermore, the myd118 polynucleotide sequences disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Polynucleotide Sequences Related to Myd118

The nucleic acid sequence for myd118 can also be used to generate hybridization probes as previously described, for mapping the endogenous genomic sequence. The sequence may be mapped to a particular chromosome or to a specific region of the chromosome using well known techniques. These include in situ hybridization to chromosomal spreads (Verma et al (1988) *Human Chromosomes: A Manual of Basic Techniques*, Pergamon Press, New York City), flow-sorted chromosomal preparations, or artificial chromosome constructions such as YACs, bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc between normal, carrier or affected individuals.

Pharmaceutical Compositions

The present invention relates to pharmaceutical compositions which may comprise all or portions of myd118 polynucleotide sequences, MYD118 polypeptides, inhibitors or antagonists of MYD118 bioactivity, including antibodies, alone or in combination with at least one other agent, such as stabilizing compound, and may be administered in any sterile, biocompatible pharmaceutical carrier, including, but not limited to, saline, buffered saline, dextrose, and water.

Myd118 nucleotide and MYD118 amino acid sequences can be administered to a patient alone, or in combination with other nucleotide sequences, such as nucleotide sequences encoding tumor suppressor genes, such as p53, p16 and p21, drugs or hormones or in pharmaceutical compositions where it is mixed with excipient(s) or other pharmaceutically acceptable carriers. In one embodiment of the present invention, the pharmaceutically acceptable carrier is pharmaceutically inert. A preferred route of administration for treatment of myeloproliferative diseases or leukemias would be intravenous delivery whereas a preferred route of administration for treatment of conditions related to inflammation would be local administration at the site of inflammation, such as the joint affected in rheumatoid arthritis.

Myd118 polynucleotide sequences or MYD118 amino acid sequences may be administered alone to individuals subject to myeloproliferative diseases or leukemias or in combination with other types of agents or therapy including chemotherapy, radiation therapy or stem cell transplant therapy.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art.

The pharmaceutical compositions can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of MYD118 may be that amount that ameliorates the symptoms of anemia, fatigue, splenomegaly, hypermetabolism and thrombohemorrhagic complications. Determination of effective amounts is well within the capability of those skilled in the art, especially in light of the disclosure provided below.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, eg, by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of MYD118, conditions indicated on the label may include treatment of myeloproliferative diseases or leukemias.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts MYD118 levels.

A therapeutically effective dose refers to that amount of MYD118 which ameliorates symptoms of the disease state. Toxicity and therapeutic efficacy of such compounds can be determined by standard pharmaceutical procedures in cell cultures or experimental animals, eg, for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds which exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for MYD118 than for the inhibitors of MYD118. Administration to the bone marrow may necessitate delivery in a manner different from intravenous injections.

These examples are provided by way of illustration and are not included for the purpose of limiting the invention.

EXAMPLES

I Construction of fetal spleen cDNA library (SPLNFET01) and Isolation of cDNA Clones The human spleen cell cDNA library was custom constructed by Stratagene (Stratagene, 937205. Torrey Pines Rd., La Jolla, Calif. 92037). The starting cell population was mixed, having been obtained from fetal spleens which have a diverse cell population. Furthermore, the fetal spleens have been pooled from different sources. Poly(A+) RNA (mRNA) was purified from the spleen cells. cDNA was synthesized from the mRNA. Synthetic adaptor oligonucleotides were ligated onto cDNA ends enabling its insertion into Uni-ZAP™ vector system (Stratagene), allowing high efficiency unidirectional (sense orientation) lambda library construction and the convenience of a plasmid system with blue/white color selection to detect clones with cDNA insertions. Alternative unidirectional vectors are pcDNA1 (Invitrogen) and pSHIox-1 (Novagen).

The custom-constructed library phage particles were transfected into *E. coli* host strain XL1-Blue® (Stratagene), which has a high transformation efficiency, increasing the probability of obtaining rare, under-represented clones in the cDNA library.

The phagemid forms of individual cDNA clones were obtained by the in vivo excision process, in which the host bacterial strain was coinfected with both the lambda library phage and an f1 helper phage. Proteins derived from both the library-containing phage and the helper phage nicked the lambda DNA, initiated new DNA synthesis from defined sequences on the lambda target DNA and created a smaller, single stranded circular phagemid DNA molecule that included all DNA sequences of the pBluescript® plasmid and the cDNA insert. The phagemid DNA was secreted from the cells and purified, then used to re-infect fresh host cells, where the double stranded phagemid DNA was produced. Because the phagemid carries the gene for β-lactamase, the newly-transformed bacteria were selected on medium containing ampicillin.

Phagemid DNA was purified using the QIAwell-8 Plasmid Purification System from QIAGEN®, QIAwell PLUS, or QIAwell ULTRA DNA Purification System (QIAGEN Inc., 9259 Eton Ave., Chattsworth, Calif. 91311). This product line provides a convenient, rapid and reliable high-throughput method to lyse bacterial cells and isolate highly purified phagemid DNA using QIAGEN anion-exchange resin particles with EMPORE™ membrane technology from 3M in a multiwell format. The DNA was eluted from the purification resin already prepared for DNA sequencing and other analytical manipulations.

The cDNA inserts from random isolates of the SPLN-FET01 library were sequenced in part.

II Homology Searching of cDNA Clones and Their Deduced Proteins

Each cDNA was compared to sequences in GenBank using a search algorithm d incorporated into the ABI INHERIT™ 670 Sequence Analysis System (Perkin Elmer, Norwalk Conn.). In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

BLAST, which stands for Basic Local Alignment Search Tool (Altschul S F (1993) J Mol Evol 36:290–300; Altschul, SF et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

MYD118 was identified using the ABI INHERITT™ DNA Analysis System (Perkin Elmer, Norwalk, Conn.) software which identified clone 25214 as being related to human GADD45 and murine MYD118. PCR extension analysis was performed to determine the 5' coding region. The nucleotide sequence for clone 25214 was subjected to a confirmatory DNA sequence analysis. The polynucleotide and amino acid sequence of MYD 118 are disclosed herein in FIG. 1 (SEQ ID NO:1) and (SEQ ID NO:2), respectively.

III Determination of Reading Frame of cDNA Clone

The reading frame of individual cDNA clones obtained from the SPLNFET01 library was obtained by analyzing the polynucleotide sequences for the presence of start (ATG, GTG, etc.) and stop codons (TGA, TAA, TAG). Typically, one frame will continue throughout the major portion of all of a cDNA sequence and the other two pending frames tend to contain numerous stop codons. Algorithms for determining reading frame have been developed which analyze the occurrence of individual nucleotide bases of each putative codon triplet (e.g., Fickett, J. W. Nucleic Acids Research, 10, 5303 (1982)). Coding DNA tends to contain predominantly certain nucleotides within certain triplet periodicities, such as a significant preference for pyrimidines in the third codon position. These algorithms have been incorporated into widely available software and can be easily used to determine coding potential (and frame) of a given stretch of DNA. This algorithm-derived information, combined with start/stop codon information, was used to determine proper frame of individual clones within the SPLNFET01 library with a high degree of certainty, thus permitting the correct reading frame alignment with appropriate expression vehicles.

IV Extension of Myd118 to Recover Regulatory Elements

The nucleic acid sequence of myd118 may be used to design oligonucleotide primers for obtaining full length sequences from genomic libraries. One primer is synthesized to initiate extension in the antisense direction (XLR) and the other is synthesized to extend sequence in the sense direction (XLF). The primers allow the known myd118 sequence to be extended "outward" generating amplicons containing new, unknown nucleotide sequence for the control region of interest. The initial primers are designed from the cDNA using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

A human genomic library is used to extend and amplify 5' upstream sequence. If necessary, a second set of primers is designed to further extend the known region. By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 $\mu$l aliquot of the reaction mixture is analyzed by electrophoresis on a low concentration (about 0.6–0.8%) agarose mini-gel to determine which reactions were successful in extending the sequence. The largest products or bands were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 $\mu$l of ligation buffer, 1 $\mu$lT4-DNA ligase (15 units) and 1

μT4 polynucleotide kinase are added, and the mixture is incubated at room temperature for 2–3 hours or overnight at 16° C. Competent E coli cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2x Carb. The following day, several colonies are randomly picked from each plate and cultured in 150 μl of liquid LB/2xCarb medium placed in an individual well of an appropriate, commercially-available, sterile 96-well microtiter plate. The following day, 5 μl of each overnight culture is transferred into a non-sterile 96-well plate and after dilution 1:10 with water, 5 μll of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:
Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

V Labeling of Hybridization Probes

Hybridization probes derived from SEQ ID NO:1 may be employed to screen cDNAs, mRNAs or genomic DNAs. Although the labeling of oligonucleotides, consisting of about 20 base-pairs, is specifically described, essentially the same procedure may be used with larger cDNA fragments. Oligonucleotides are labeled by combining 50 pmol of each oligomer and 250 mCi of [γ-$^{32}$P] adenosine triphosphate (Amersham, Chicago Ill.) and T4 polynucleotide kinase (DuPont NEN®, Boston Mass.). The labeled oligonucleotides are purified with Sephadex G-25 super fine resin column (Pharmacia). A portion containing 107 counts per minute of each is used in a typical membrane based hybridization analysis of human genomic DNA digested with one of the following endonucleases (Ase I, Bgl II, EcoR I, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VI Antisense Molecules

The myd118 sequence, or any part thereof, may be used to inhibit in vivo or in vitro expression of endogenous Myd118. Although use of antisense oligonucleotides, consisting of about 20 base-pairs, is specifically described, essentially the same procedure may be used with larger cDNA fragments. An oligonucleotide based on the coding sequence of myd118 may be used to inhibit expression of endogenous Myd118. Using Oligo 4.0, the complementary oligonucleotide can be designed from the conserved 5' sequence and used either to inhibit transcription by preventing promoter binding to the upstream nontranslated sequence or translation of an myd118 transcript by preventing the ribosome from binding to the mRNA.

VII Production of MYD118 Specific Antibodies

For production of polyclonal antibodies, the deduced amino acid sequence of MYD118 is analyzed using DNASTAR software (DNASTAR Inc) to determine regions of high immunogenicity and a corresponding oligopeptide is synthesized and used to raise antibodies in rabbits. Analysis to select appropriate epitopes, such as those near the C-terminus or in adjacent hydrophilic regions is described by Ausubel FM et al (supra). An oligopeptide of about 15 residues in length is synthesized using an ABI Peptide Synthesizer Model 431A (Perkin Elmer, Norwalk, Conn.) using fmoc-chemistry, and coupled to keyhole limpet hemocyanin (KLH, Sigma) by reaction with M-maleimidobenzoyl-N-hydroxysuccinimide ester (MBS; Ausubel FM et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

VIII Purification of MYD118 Using Specific Antibodies

Endogenous or recombinant MYD118 can be purified by immunoaffinity chromatography using antibodies specific for MYD118. An immunoaffinity column is constructed by covalently coupling MYD118 antibody to an activated chromatographic resin such as CnBr-activated Sepharose (Pharmacia Biotech). After the coupling, the resin is blocked and washed according to the manufacturer's instructions.

Media containing MYD118 is passed over the immunoaffinity column, and the column is washed under conditions that allow the preferential absorbance of MYD118 (eg, high ionic strength buffers in the presence of detergent). The column is eluted under conditions that disrupt antibody/MYD118 binding (eg, a buffer of pH 2–3 or a high concentration of a chaotrope such as urea or thiocyanate ion), and MYD118 is collected.

IX Identification of Molecules Which Interact with Myd118

MYD118, or biologically active fragments thereof, are labeled with $^{125}$I Bolton-Hunter reagent (Bolton, A E and Hunter, W M (1973) Biochem J 133: 529). Candidate small molecules previously arrayed in the wells of a 96 well plate are incubated with the labeled MYD 118, washed and any wells with labeled MYD118 complex are assayed. Data obtained using different concentrations of MYD118 are used to calculate values for the number, affinity, and association of MYD118 with the candidate molecules.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polypeptide comprising an amino acid sequence selected from the group consisting of
   a) an amino acid sequence of SEQ ID NO:2, and,
   b) an antigenically-active fragment of the amino acid sequence of SEQ ID NO:2.

2. A polypeptide of claim 1 comprising the amino acid sequence of SEQ ID NO:2.

3. A composition comprising a polypeptide of claim 2 and a pharmaceutically acceptable excipient.

4. A composition comprising a polypeptide of claim 1 and a pharmaceutically acceptable excipient.

* * * * *